United States Patent [19]

Ripamonti

[11] Patent Number: 5,443,531
[45] Date of Patent: Aug. 22, 1995

[54] DELIVERY SYSTEM FOR BIOLOGICALLY ACTIVE GROWTH OR MORPHOGENETIC FACTORS AND TO A METHOD FOR PREPARING SUCH A DELIVERY SYSTEM

[75] Inventor: Ugo Ripamonti, Johannesburg, South Africa

[73] Assignee: South African Medical Research Council, South Africa

[21] Appl. No.: 875,368

[22] Filed: Apr. 29, 1992

[30] Foreign Application Priority Data

Apr. 29, 1991 [ZA] South Africa ............ 91/3225

[51] Int. Cl.$^6$ .............................................. A61F 2/02
[52] U.S. Cl. ....................................................... 623/66
[58] Field of Search ............. 623/1, 16, 66; 424/422, 424/423; 514/21

[56] References Cited

U.S. PATENT DOCUMENTS

| | | |
|---|---|---|
| 3,929,971 | 12/1975 | Roy . |
| 4,294,753 | 10/1981 | Urist . |
| 4,546,500 | 10/1985 | Bell ........................ 623/1 |
| 4,596,574 | 6/1986 | Urist ...................... 623/16 |
| 4,627,982 | 9/1986 | Seyedin et al. . |
| 4,925,669 | 5/1990 | Dyer . |
| 5,010,009 | 4/1991 | Steele et al. ............ 623/1 |
| 5,035,708 | 7/1991 | Alchas et al. .......... 623/1 |
| 5,106,626 | 4/1992 | Parsons et al. ........ 623/16 |
| 5,108,436 | 4/1992 | Chu et al. .............. 623/16 |
| 5,154,931 | 10/1992 | Krüger . |

FOREIGN PATENT DOCUMENTS

WO8910409 11/1989 WIPO .
WO9011366 10/1990 WIPO .

OTHER PUBLICATIONS

Y. Horisaka, et al; "Subperiosteal Implantation of Bone Morphogenetic Protein Adsorbed by Hydroxyapatite"; Jul. 1991; Clinical Opthopaedics and Related Research No. 268; pp. 303–311.

M. Urist, et al; "Purification of Bovine Bone Morphogenetic Protein by Hydroxyapatite Chromatography"; Proceedings of the National Academy of Sciences of the U.S. of A. vol. 81, Jan. 1984; pp. 371–375.

T. K. Sampath, et al; "Isolation of Osteogenin, an Extracellular Matrix-associated, Bone-inductive Protein, by Herparin Affinity Chromatography", Oct. 1987; Proc. Natl. Acad. Sci. USA, vol. 84, pp. 7109–9113.

Frank Luyten, et al; "Purification and Partial Amino Acid Sequence of Osteogenin, a Proteen Initiating Bone Differentiation"; Aug. 15, 1989; The Journal of Biological Chemistry, vol. 264, pp. 13377–13380.

U.S. patent application Ser. No. 07/720,174 filed Jun. 27, 1991 to U. Ripamonti.

*Primary Examiner*—David Isabella

[57] ABSTRACT

A method of preparing a delivery system for a biologically active growth and morphogenetic factor by using chromatographic techniques and which includes introducing such biologically active factor into a chromatography column of appropriate dimensions which contains a porous carrier comprising a solid adsorbent selected for its specific affinity for such biologically active factor. In one embodiment of the invention porous hydroxyapatite is used as the carrier for bone morphogenetic proteins (ie BMPs). The invention extends to a delivery system prepared according to the above method; to an apparatus for preparing the delivery system according to the method; and to use of the delivery system in a method for inducing the formation of new bone in primates.

4 Claims, 4 Drawing Sheets

DELIVERY SYSTEM FOR BIOLOGICALLY ACTIVE GROWTH OR MORPHOGENETIC FACTORS AND TO A METHOD FOR PREPARING SUCH A DELIVERY SYSTEM

This invention relates to a delivery system for biologically active growth or morphogenetic factors and to a method for preparing such a delivery system.

According to the invention there is provided a method of preparing a delivery system for biologically active growth or morphogenetic factors, by using chromatographic techniques and which includes introducing such biologically active factors into a chromatography column which contains a porous carrier comprising an adsorbent selected for its specific affinity for such biologically active factors.

Needless to say, the chromatography column will be of appropriate dimensions, easily determinable by a person of ordinary skill in the art.

The biologically active factor may be, for example, a bone morphogenetic protein for inducing new bone formation, and then a preferred porous carrier is porous hydroxyapatite.

Adsorption of the biologically active growth or morphogenetic factors onto the carrier can be controlled by the method of the invention, for example by controlling the rate of ingress of the biologically active factor into the chromatography column. This may be achieved via a capillary tube in communication with a supply of the biologically active factor dissolved or suspended in a suitable vehicle therefor.

Further, according to the invention, there is provided a delivery system for bone morphogenetic proteins (i.e. BMPs) including BMP-3 (osteogenin) for inducing new bone formation, which delivery system comprises a porous carrier comprising an adsorbent selected for its specific affinity for the proteins and onto which the bone morphogenetic proteins have been adsorbed by introducing the proteins into a chromatography column containing the porous carrier.

A preferred delivery system according to the invention comprises porous hydroxyapatite onto which the BMPs have been adsorbed.

Suitable porous hydroxyapatite for the carrier may be obtained, by conventional techniques, after hydrothermal conversion of calcium carbonate exoskeletons of corals.

The applicant envisages that the osteogenin- and/or the related BMPs-hydroxyapatite delivery system will be of particular importance in the use thereof for inducing new bone formation in primates including man.

The invention extends to a delivery system according to the invention for use in a method of inducing the formation of new bone in primates, said delivery system comprising a porous carrier onto which appropriate BMPs have been adsorbed by introducing the BMPs into a chromatography column containing the porous carrier selected for its specific affinity for the BMPs, and said method comprising implanting the delivery system into that region in the body of the primate, where bone is required.

The invention further extends to a method according to the invention for preparing a delivery system for use in a method of inducing formation of new bone in a primate. It will be appreciated that this method can have significant therapeutic application.

The invention extends yet further to a method of inducing the formation of new bone in primates, which includes implanting into that region in the body of the primate where bone is required, a delivery system comprising a porous carrier onto which a bone morphogenetic protein has been adsorbed by introducing the protein into a chromatography column containing the porous carrier selected for its specific affinity for the protein.

According to another aspect of the invention there is provided an apparatus for preparing a delivery system for a biologically active growth or morphogenetic factor, which apparatus includes
a chromatography column for accommodating a porous carrier comprising an adsorbent having a specific affinity for the biologically active factor; and
a control means at or adjacent the inlet end of the column for controlling the rate of ingress into the column, of the biologically active factor.

The control means may comprise a capillary tube for connecting a supply of the biologically active factor dissolved or suspended in a suitable vehicle therefor, to the chromatography column via the inlet end thereof.

The extracellular matrix of bone in the form of insoluble collagenous carrier after dissociative extraction with 4M guanidine hydrochloride or 6M urea has been shown to optimize the induction of local endochondral bone differentiation when reconstituted with BMPs, a family of protein initiators of bone formation [1,2]. Significant challenges to their delivery, however, still limits the utilization of BMPs as therapeutic agents for the controlled formation of new bone in man. The necessity of using the insoluble collagenous carrier limits the clinical application of the phenomenon of bone induction, since the organic component prepared from human bone matrix may retain alloantigens as well as transmittable viruses such as human immunodeficient virus and hepatitis B virus. An inorganic, nonimmunogenic delivery system for BMPs is needed for the therapeutic application of the phenomenon of bone induction in skeletal reconstruction. This would reduce and may even obviate the need for surgical harvest of autogenous bone and related morbidity.

The numbers in square brackets identify the relevant references in the list of references.

The invention is now described by way of the following non-limiting example and with reference to the accompanying drawings in which FIG. 1 is a schematic drawing of an apparatus according to the invention and comprising a column for liquid chromatography, and related apparatus used for adsorbing BMPs onto porous hydroxyapatite carriers according to the method of the invention; related apparatus used for adsorbing BMPs onto porous hydroxyapatite carriers according to the method of the invention;

It should be understood that it is solely for descriptive purposes that the invention is illustrated using BMP fractions isolated from the extracellular matrix of baboon bone and adsorbed on porous hydroxyapatite carrier discs, 25 mm in diameter and 3.5 mm in thickness, and that the invention should not be construed as being limited thereto.

Figure 1:
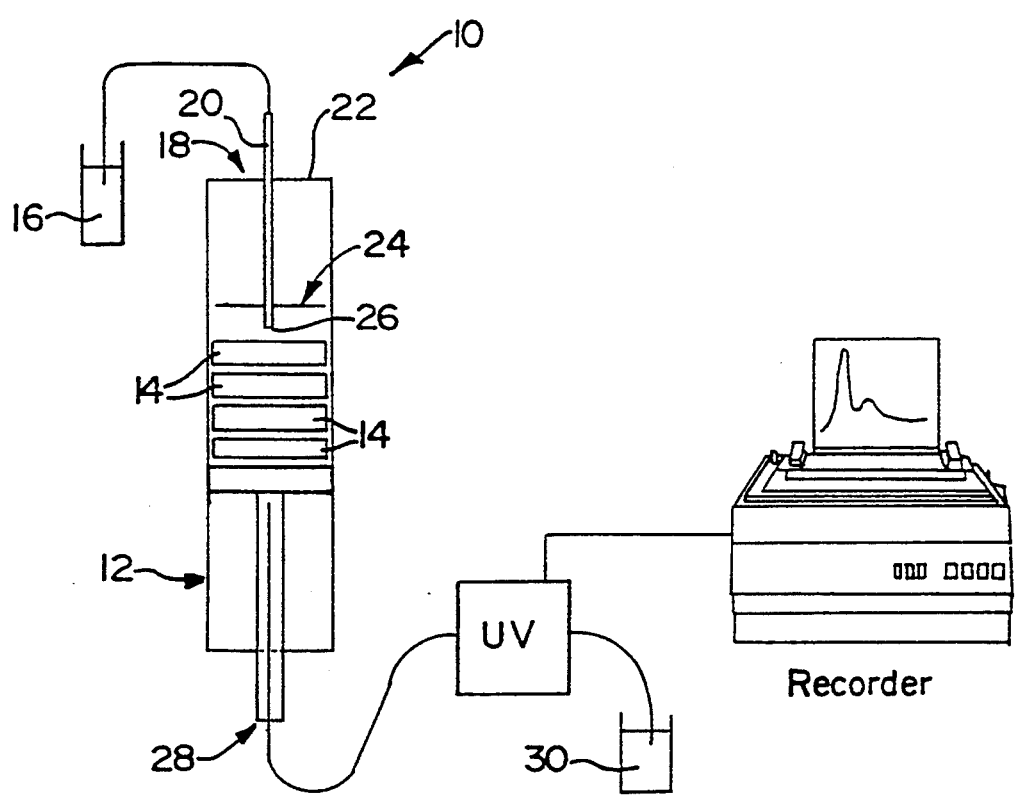

Referring now to FIGS. 1–7 of the drawings,

FIG. 1 shows biologically active BMPs fractions, as determined by alkaline phosphatase activity and histology, are loaded onto porous hydroxyapatite carrier discs 14 placed within a standard column for liquid chromatography. Loading and subsequent adsorption of BMPs fractions is facilitated by a modification of the column inlet 18. This modification consists in connecting the column inlet 18 to a capillary tube 20, 2 mm in diameter, in plastic or glass to the top end sealing piece 22 of the column. The level 24 of the starting buffer (5 mM HCl) is regulated as to be 10 mm above the tip 26 of the capillary tube 20.

Figure 2:
FIGS. 2 to 4 are photomicrographs of histological sections through implants comprising the delivery system of the invention, and harvested 30 days after implantation.

FIG. 2 shows a photomicrograph of a central area of the osteogenic delivery system. There is extensive bone formation within the porous spaces of the carrier disc harvested 30 days after intramuscular implantation in a male baboon. White empty spaces represent the hydroxyapatite framework dissolved after histological processing and decalcification of the specimen.

Figure 3:
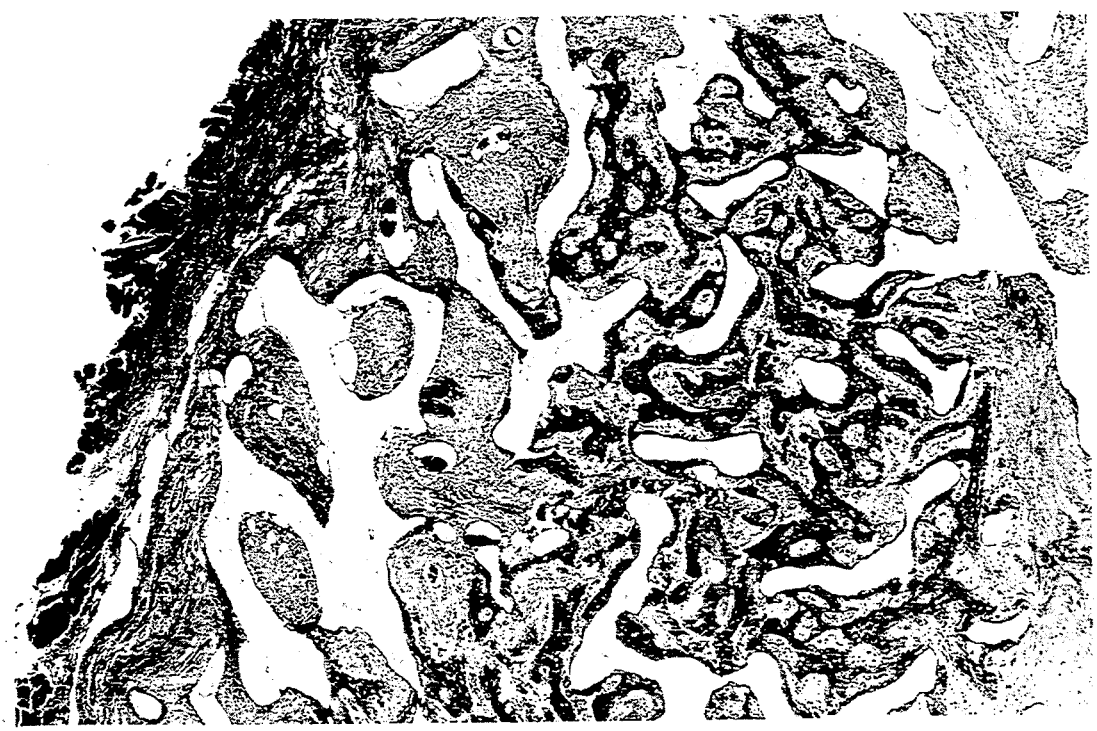

FIG. 3 shows a photomicrograph of a peripheral area of the osteogenic delivery system. There is bone formation within the porous spaces of the carrier disc harvested 30 days after intramuscular implantation in a male baboon. Note the muscular tissue (left) surrounding the osteogenic delivery system.

Figure 4:
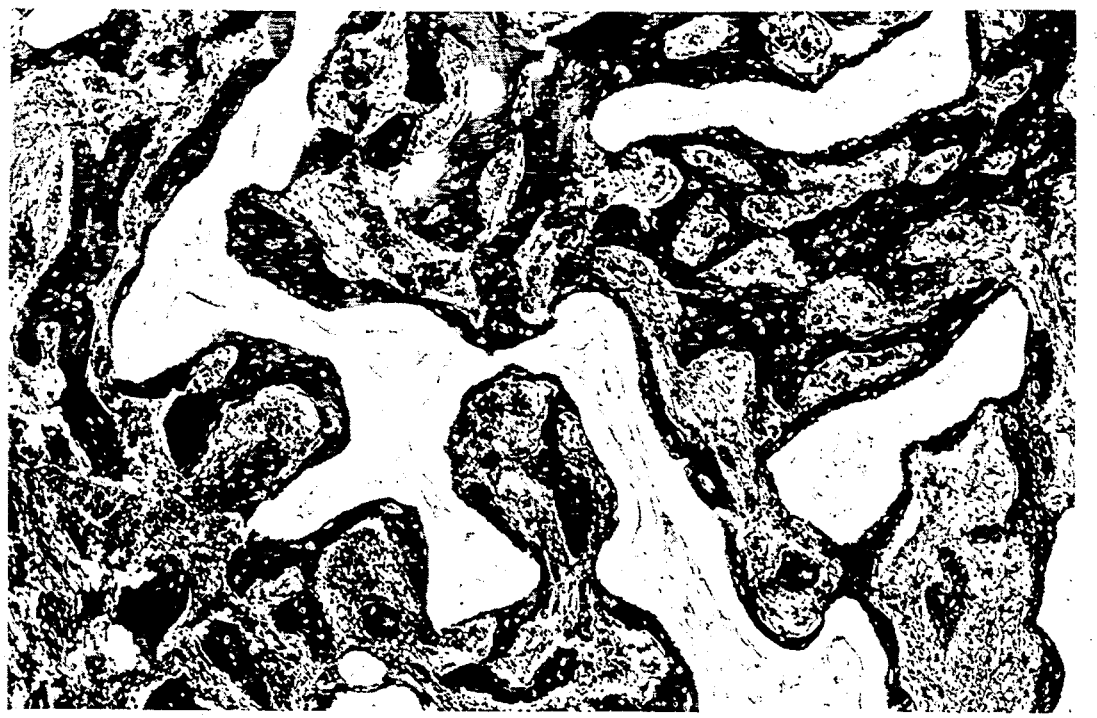

FIG. 4 shows a high power photomicrograph of the osteogenic delivery system. There is extensive bone formation within the porous spaces of the carrier disc. Note the pronounced cellularity and vascularity of the newly formed bone.

Figure 5:
FIG. 5 is a photomicrograph of a histological section through a control implant comprising a porous hydroxyapatite carrier onto which no BMPs had been adsorbed.

FIG. 5 shows a photomicrograph of a central region of a porous hydroxyapatite disc implanted in a male baboon without prior adsorption of BMPs fractions. Note the limited cellular and vascular invasion within the porous spaces and the lack of bone formation.

Figure 6:
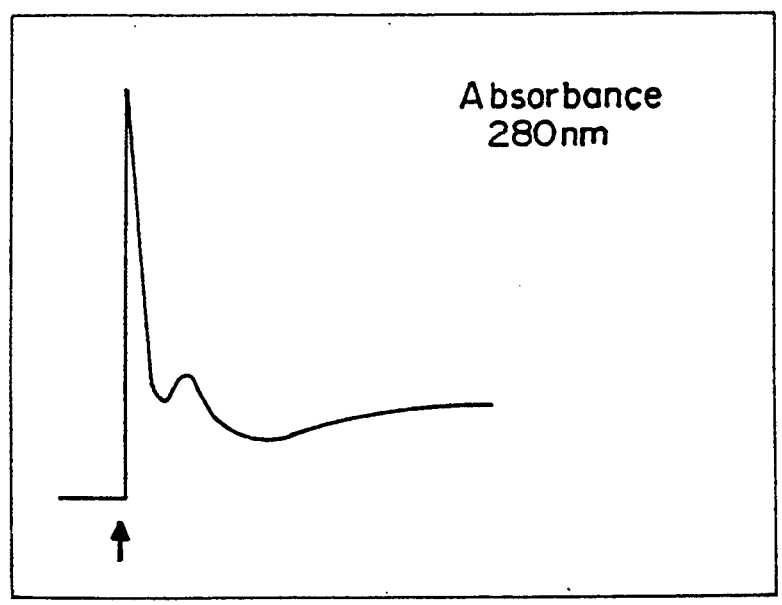
FIG. 6 is a chromatographic profile of BMP fractions on porous hydroxyapatite carriers.

FIG. 6 shows a chromatographic profile of BMPs fractions on porous hydroxyapatite discs. Arrow indicates loading of the biologically active BMPs fractions in 5 mM HCl.

Figure 7:
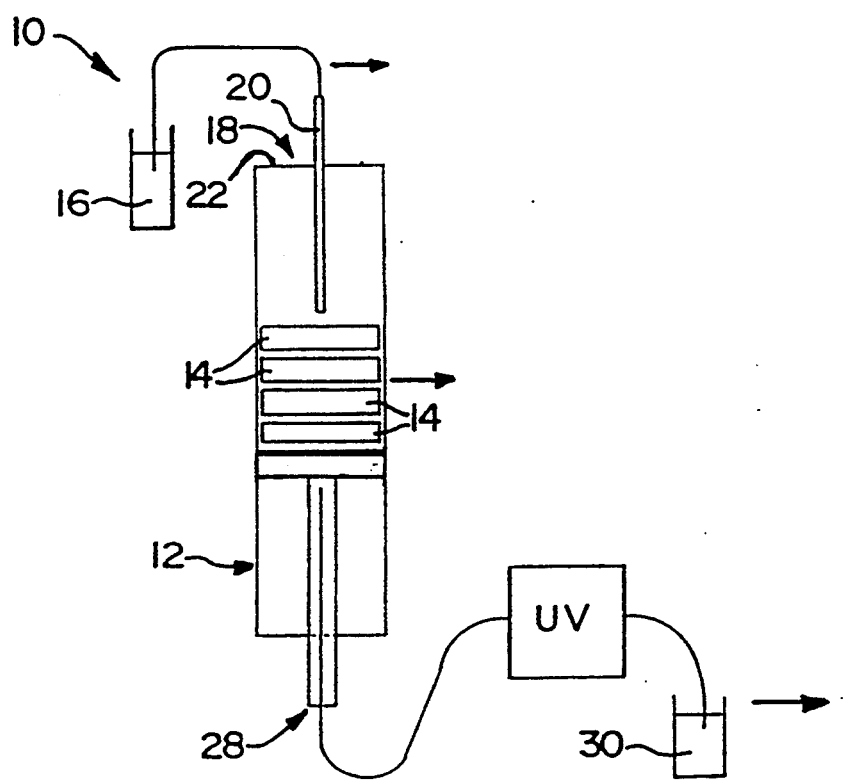
FIG. 7 is a schematic drawing showing three bioassays used to test the biological activity of the invention.

FIG. 7 shows a schematic representation of the bioassays performed to test the osteogenic property of the delivery system. Arrow A indicates the point at which BMPs fractions are taken, before chromatography, for testing in the subcutaneous space of the rat. Arrow B indicates that the osteogenic delivery system is taken after adsorption chromatography of BMPs fractions for intramuscular placement in primates. Arrow C indicates that unbound material (eluate) is taken after the chromatography step for placement in the subcutaneous space of the rat.

Hydroxyapatite Carriers: Description and Specifications

Implant carriers consisting of porous non-degradable hydroxyapatite were obtained in disc form, 25 mm in diameter and 3.5 mm in thickness. The solid components of the framework average 130 $\mu$m in diameter and their interconnections average 220 $\mu$m in diameter. The average porosity is 600 $\mu$m and their interconnections average 260 $\mu$m in diameter (Interpore 500 Interpore International, Irvine, Calif., U.S.A.). The hydroxyapatite is obtained after hydrothermal chemical exchange with phosphate converting the original calcium carbonate exoskeletal microstructure of the scleractinian reef-building coral of the genus Goniopora [5] into an inorganic replica of hydroxyapatite [6–8]. Conversion to hydroxyapatite is monitored by X-ray diffraction pattern, showing that hydroxyapatite replicas consist of 90 percent hydroxyapatite and 10 percent tricalcium phosphate.

Purification and Preparation of Baboon BMP Fractions

Dehydrated diaphyseal baboon bone matrix, sieved to a discrete particle size of 74–420 $\mu$m, was demineralized in 0.5N HCl and dissociatively extracted in 4M guanidine-HCl, 50 mM Tris, pH 7.4, containing protease inhibitors [1]. Baboon BMPs were isolated using methods in reference 1, and as described for the purification of BMP-3(osteogenin) from baboon bone matrix [4]. After gel filtration chromatography, BMP fractions were tested as follows, for biological activity in the subcutaneous space of a rat. Osteogenic activity is tested by reconstituting 25 mg of rat insoluble collagenous bone matrix (the inactive carrier obtained after dissociative extraction of rat bone matrix) with 5 to 20 $\mu$g of BMP fractions as described [1,4]. After implantation in the subcutaneous space of the rat, implants were harvested at day 11 and examined biochemically (alkaline phosphatase activity) and histologically.

Controlled Adsorption and Binding of BMP Fractions onto Hydroxyapatite Carrier: Creation of the Osteogenic Delivery System Aspects of the invention are illustrated in the following two steps: 1: adsorption of BMPs onto porous hydroxyapatite carrier using liquid chromatography techniques to provide a delivery system according to the invention, and 2: the use of this delivery system to deliver BMPs and to induce the formation of new bone after in vivo implantation in primates.

1. Adsorption chromatography on hydroxyapatite carriers

The most active BMP fractions, as determined by alkaline phosphatase activity and histological evidence of florid bone formation in the subcutaneous space of the rat, were concentrated and exchanged with 5 mM hydrochloric acid (HCl) using ultrafiltration membranes with 10,000 mw cutoff (Amicon, YM-10). Prior to adsorption onto hydroxyapatite discs, aliquots of osteogenin fractions in 5 mM HCl were tested for biological activity in the subcutaneous space of the rat. In an apparatus 10 according to the invention, a liquid chromatography column 12 with an internal diameter of 25 mm, was loaded with porous hydroxyapatite carrier discs 14, 25 mm in diameter (FIG. 1). The column was equilibrated with starting buffer (5 mM HCl). After equilibration, BMP fractions, dissolved in 5 ml of starting buffer 16, were loaded onto the porous hydroxyapatite carrier discs 14, thereby providing delivery systems according to the invention for implantation. Loading and subsequent adsorption of BMP fractions was facilitated by a modification of the column inlet 18. This modification comprised connecting the column inlet 18 to a capillary tube 20, 2 mm in diameter, in plastic or glass located through the top end sealing piece 22 of the column 12. The level 24 of the starting buffer was regulated so as to be 10 mm above the tip 26 of the capillary tube 20.

After loading, the capillary outlet 28 of the column 12 was connected with the column inlet providing a continuous recirculation of starting buffer and unbound material (FIG. 1). Reference numeral 30 indicates the eluate. In a preferred embodiment, at least a portion of the eluate 30 from outlet 28 is diverted for analysis 40 in order to determine the unbound fraction. The data may be recorded on an appropriate recording device 42. After stabilization of unbound fractions on the chromatographic profile (FIG. 6), unbound fractions were collected in 20 ml of starting buffer (column capacity) for testing their biological activity in the subcutaneous space of the rat in the manner described above. After recovery of the unbound material in starting buffer, the BMPs-hydroxyapatite carrier discs 14 were left to dry in a laminar flow cabinet at room temperature.

In Vivo Bioassay of the Osteogenic Delivery System (FIG. 7)

The in vivo bioassay consisted of the following three steps: 1: bioassay of the BMP fractions before loading the hydroxyapatite carrier discs; 2: bioassay of the osteogenic delivery system in primates of the genus Papio (baboon, Papio ursinus); and 3: bioassay of unbound protein fractions to determine residual biological activity, if any, in the unbound material.
1. BMP fractions were tested for biological.
2. BMPs-hydroxyapatite carrier discs were implanted intramuscularly in male baboons to test the osteogenic activity of the delivery system. Bone formation within the hydroxyapatite discs was assessed histologically after harvesting the implants 30 days after surgical implantation. For the purpose of testing its osteogenic potential, the delivery system was implanted in extraskeletal sites to provide unequivocal proof that any bone formation was induced by BMPs delivered during healing and incorporation, by the hydroxyapatite carrier.

FIG. 2 shows extensive bone formation within the porous spaces of a hydroxyapatite carrier disc after adsorption chromatography of biologically active BMP fractions, and harvested 30 days after being implanted intramuscularly in a male baboon. The white empty spaces evident in FIG. 2 represent the hydroxyapatite framework dissolved after histological processing and decalcification of the specimen.

FIG. 3 shows extensive vascular invasion and bone differentiation in a peripheral area of a hydroxyapatite carrier disc after adsorption chromatography of biologically active BMP fractions, and harvested 30 days after being implanted intramuscularly in a male baboon. Attention is drawn, in particular, to the muscular tissue (left) surrounding the osteogenic delivery system.

FIG. 4 shows details of the newly formed bone within the porous spaces of the hydroxyapatite carrier disc after adsorption chromatography of biologically active BMP fractions. As can be seen, extensive bone formation has occurred within the porous spaces of the carrier disc. The pronounced cellularity and vascularity of the newly formed bone should be noted.

Discs of hydroxyapatite carriers were implanted without chromatographic adsorption of BMPs, as control. FIG. 5 shows limited penetration of fibrovascular and cellular elements and lack of bone differentiation.
3. Possible residual biological activity in the unbound fraction collected from the column after adsorption chromatography was assessed by reconstituting 25 mg of rat insoluble collagenous carrier with increasing concentration of unbound protein fractions. No bone differentiation occurred in implants reconstituted with 50, 200, 500, 1000 and 2000 $\mu$l respectively of unbound material.

These results demonstrate the osteogenic properties of the invention after chromatographic adsorption of BMP fractions onto porous hydroxyapatite carriers and implantation in extraskeletal sites of primates.

It will be understood that it is intended to cover all changes and modification of the description of the invention herein disclosed for the purpose of illustration which do not constitute departures from the spirit and scope of the invention. In particular, the chromatographic technique is not limited to the adsorption of BMPs (including both native and human recombinant material), but extends to other biologically active cellular modulators such as laminin, type IV collagen, transforming growth factors beta, insulin growth factor II, platelet derived growth factor, fibroblast growth factor(s), and growth hormone. In addition, the porous material used as carrier is not limited to hydroxyapatite replicas, but includes a variety of other porous biomaterials, such as sintered hydroxyapatites, polymers, plasma-sprayed hydroxyapatite titanium porous implants and alloys for skeletal reconstruction, and other biomaterials such as collagenic carriers, artificial skins and the like for the controlled adsorption and binding of growth or morphogentic factors for soft tissue reconstruction.

REFERENCES

1. Luyten F. P., Cunningham N. S., Ma S., Muthukumaran N., Hammonds R. G., Nevins W. B., Wood W. I., Reddi A. H. (1989) Purification and partial amino acid sequence of osteogenin, a protein initiating bone differentiation. J Biol Chem 264:13377–13380.
2. Wozney J. M. et al; Novel regulators of bone formation: Molecular clones and activities. Science 242:1528–1534, 1988.
3. Ripamonti U. (1991). Bone induction in nonhuman primates. An experimental study on the baboon. Clin Orthop Rel Res, 269 col 284–294.
4. Ripamonti U., Ma S., Cunningham N., Yates L., Reddi A. H. (1992). Initiation of bone regeneration in adult baboons by osteogenin, a bone morphogenetic protein. Matrix, in press.
5. Wells J. W. (1956) Scleractinia. In: Moore RC (ed) Treatise on Invertebrate Paleontology. University of Kansas Press, Kansas City, p 328–444.
6. Weber J. N., White E. W. (1973) Carbonate minerals as precursors of new ceramics, metal, and polymer materials for biomedical applications. Miner Sci Engng 5:151–165.
7. Roy D. M., Linnehan S. K. (1974) Hydroxyapatite formed from coral skeletal carbonate by hydrothermal exchange. Nature 247:220–222.
8. White E. W., Weber J. N., Roy D. M., Owen E. L. (1975) Replamine-form porous biomaterials for hard tissue implant applications. J Biomed Mater Res Symposium 6:23–27.

I claim:

1. A method of preparing a delivery system for a biologically active growth or morphogenic factor, comprising the steps of
   (a) providing, in a chromatography column, a porous carrier comprising an adsorbent selected for its specific affinity for such biologically active factor,
   (b) dissolving or suspending the biologically active factor in a suitable fluid vehicle therefor, (c) introducing into the column above the carrier the vehicle carrying the biologically active factor at a controlled rate, (d) contacting the biologically active factor with the porous carrier in the column so that the factor is adsorbed onto the carrier, (e) collecting the non-adsorbed fraction of the biologically active factor carried in the vehicle from the column at a point below the carrier, (f) analyzing the non-adsorbed fraction to determine the saturation state of the carrier, and (g) until saturation of the carrier is reached, returning the non-adsorbed fraction to the column and repeating steps (c) through (f).

2. The method of claim 1, wherein the biologically active factor is a bone morphogenetic protein for inducing bone formation and the porous carrier is composed of hydroxyapatite.

3. The method of claim 1, wherein step (a) further comprises providing a plurality of porous carrier disks, arranged one above the other, which disks have a diameter substantially equal to the inside diameter of the column.

4. The method as claimed in claim 18, wherein step (c) further comprises controlling the rate of introduction of the biologically active factor into the chromotography column via a capillary tube which is in communication at one end thereof with a supply of the biologically active factor dissolved or suspended in said vehicle, and is maintained at the other end thereof within the chromotography column, whereby the introduction of biologically active factor is controlled so that the fluid level thereof is maintained above said other end of the capillary tube.

* * * * *

UNITED STATES PATENT AND TRADEMARK OFFICE
CERTIFICATE OF CORRECTION

PATENT NO. : 5,443,531
DATED : August 22, 1995
INVENTOR(S) : Ripamonti

It is certified that error appears in the above-indentified patent and that said Letters Patent is hereby corrected as shown below:

The title page, showing an illustrative figure, should be deleted and substitute therefor the attached title page.

United States Patent [19]

Ripamonti

[11] Patent Number: 5,443,531
[45] Date of Patent: Aug. 22, 1995

[54] DELIVERY SYSTEM FOR BIOLOGICALLY ACTIVE GROWTH OR MORPHOGENETIC FACTORS AND TO A METHOD FOR PREPARING SUCH A DELIVERY SYSTEM

[75] Inventor: Ugo Ripamonti, Johannesburg, South Africa

[73] Assignee: South African Medical Research Council, South Africa

[21] Appl. No.: 875,368

[22] Filed: Apr. 29, 1992

[30] Foreign Application Priority Data

Apr. 29, 1991 [ZA] South Africa .................. 91/3225

[51] Int. Cl.$^6$ .................................. A61F 2/02
[52] U.S. Cl. .................................. 623/66
[58] Field of Search .............. 623/1, 16, 66; 424/422, 424/423; 514/21

[56] References Cited

U.S. PATENT DOCUMENTS

| | | |
|---|---|---|
| 3,929,971 | 12/1975 | Roy . |
| 4,294,753 | 10/1981 | Urist . |
| 4,546,500 | 10/1985 | Bell ........................ 623/1 |
| 4,596,574 | 6/1986 | Urist ....................... 623/16 |
| 4,627,982 | 9/1986 | Seyedin et al. . |
| 4,925,669 | 5/1990 | Dyer . |
| 5,010,009 | 4/1991 | Steele et al. ............. 623/1 |
| 5,035,708 | 7/1991 | Alchas et al. ............ 623/1 |
| 5,106,626 | 4/1992 | Parsons et al. .......... 623/16 |
| 5,108,436 | 4/1992 | Chu et al. ............... 623/16 |
| 5,154,931 | 10/1992 | Krüger . |

FOREIGN PATENT DOCUMENTS

WO8910409 11/1989 WIPO .
WO9011366 10/1990 WIPO .

OTHER PUBLICATIONS

Y. Horisaka, et al; "Subperiosteal Implantation of Bone Morphogenetic Protein Adsorbed by Hydroxyapatite"; Jul. 1991; Clinical Opthopaedics and Related Research No. 268; pp. 303–311.

M. Urist, et al; "Purification of Bovine Bone Morphogenetic Protein by Hydroxyapatite Chromatography"; Proceedings of the National Academy of Sciences of the U.S. of A. vol. 81, Jan. 1984; pp. 371–375.

T. K. Sampath, et al; "Isolation of Osteogenin, an Extracellular Matrix-associated, Bone-inductive Protein, by Herparin Affinity Chromatography", Oct. 1987; Proc. Natl. Acad. Sci. USA, vol. 84, pp. 7109–9113.

Frank Luyten, et al; "Purification and Partial Amino Acid Sequence of Osteogenin, a Proteen Initiating Bone Differentiation"; Aug. 15, 1989; The Journal of Biological Chemistry, vol. 264, pp. 13377–13380.

U.S. patent application Ser. No. 07/720,174 filed Jun. 27, 1991 to U. Ripamonti.

*Primary Examiner*—David Isabella

[57] ABSTRACT

A method of preparing a delivery system for a biologically active growth and morphogenetic factor by using chromatographic techniques and which includes introducing such biologically active factor into a chromatography column of appropriate dimensions which contains a porous carrier comprising a solid adsorbent selected for its specific affinity for such biologically active factor. In one embodiment of the invention porous hydroxyapatite is used as the carrier for bone morphogenetic proteins (ie BMPs). The invention extends to a delivery system prepared according to the above method; to an apparatus for preparing the delivery system according to the method; and to use of the delivery system in a method for inducing the formation of new bone in primates.

4 Claims, 4 Drawing Sheets

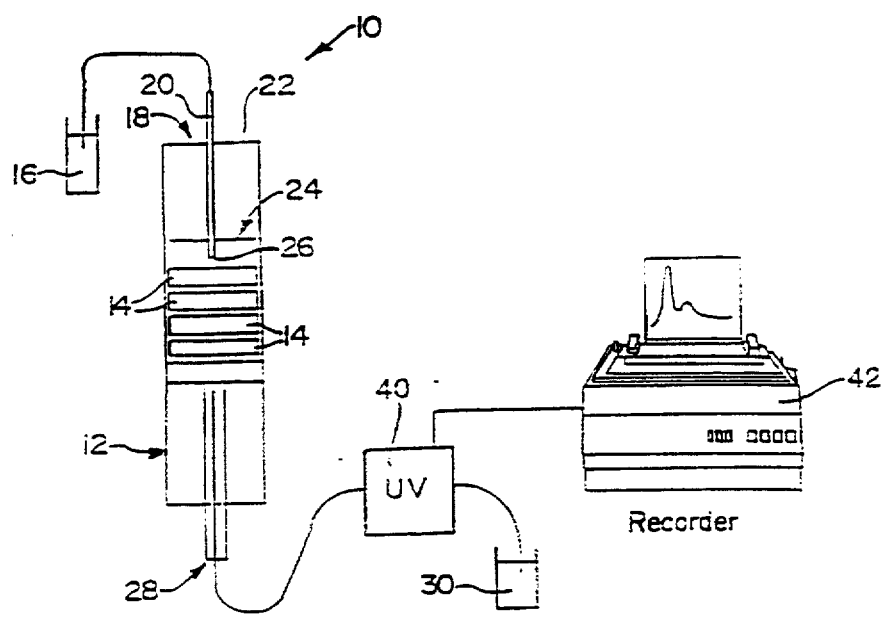

UNITED STATES PATENT AND TRADEMARK OFFICE
CERTIFICATE OF CORRECTION

PATENT NO.    :    5,443,531
DATED         :    August 22, 1995
INVENTOR(S)   :    Ugo Ripamonti It is certified that an error appears in the above-identified patent and that said Letters Patent is hereby corrected as shown below:

Column 8, line 8, should read as follows:

4. The method as claimed in claim 1, wherein step

Signed and Sealed this

Twenty-fifth Day of June, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO.   :  5,443,531
DATED        :  August 22, 1995
INVENTOR(S)  :  Ugo Ripamonti It is certified that error appears in the above-indentified patent and that said Letters Patent is hereby corrected as shown below:

The title page, showing an illustrative figure, should be deleted and substitute therefor the attached title page.

This Certificate supercedes Certificate of Correction issued June 25, 1996.

United States Patent [19]

Ripamonti

[11] Patent Number: 5,443,531
[45] Date of Patent: Aug. 22, 1995

[54] DELIVERY SYSTEM FOR BIOLOGICALLY ACTIVE GROWTH OR MORPHOGENETIC FACTORS AND TO A METHOD FOR PREPARING SUCH A DELIVERY SYSTEM

[75] Inventor: Ugo Ripamonti, Johannesburg, South Africa

[73] Assignee: South African Medical Research Council, South Africa

[21] Appl. No.: 875,368

[22] Filed: Apr. 29, 1992

[30] Foreign Application Priority Data

Apr. 29, 1991 [ZA] South Africa .............. 91/3225

[51] Int. Cl.$^6$ .................................................. A61F 2/02
[52] U.S. Cl. ...................................................... 623/66
[58] Field of Search .............. 623/1, 16, 66; 424/422, 424/423; 514/21

[56] References Cited

U.S. PATENT DOCUMENTS

| | | | |
|---|---|---|---|
| 3,929,971 | 12/1975 | Roy . | |
| 4,294,753 | 10/1981 | Urist . | |
| 4,546,500 | 10/1985 | Bell | 623/1 |
| 4,596,574 | 6/1986 | Urist | 623/16 |
| 4,627,982 | 9/1986 | Seyedin et al. . | |
| 4,925,669 | 5/1990 | Dyer . | |
| 5,010,009 | 4/1991 | Steele et al. | 623/1 |
| 5,035,708 | 7/1991 | Alchas et al. | 623/1 |
| 5,106,626 | 4/1992 | Parsons et al. | 623/16 |
| 5,108,436 | 4/1992 | Chu et al. | 623/16 |
| 5,154,931 | 10/1992 | Krüger . | |

FOREIGN PATENT DOCUMENTS

WO8910409 11/1989 WIPO .
WO9011366 10/1990 WIPO .

OTHER PUBLICATIONS

Y. Horisaka, et al; "Subperiosteal Implantation of Bone Morphogenetic Protein Adsorbed by Hydroxyapatite"; Jul. 1991; Clinical Opthopaedics and Related Research No. 268; pp. 303–311.

M. Urist, et al; "Purification of Bovine Bone Morphogenetic Protein by Hydroxyapatite Chromatography"; Proceedings of the National Academy of Sciences of the U.S. of A. vol. 81, Jan. 1984; pp. 371–375.

T. K. Sampath, et al; "Isolation of Osteogenin, an Extracellular Matrix-associated, Bone-inductive Protein, by Herparin Affinity Chromatography", Oct. 1987; Proc. Natl. Acad. Sci. USA, vol. 84, pp. 7109–9113.

Frank Luyten, et al; "Purification and Partial Amino Acid Sequence of Osteogenin, a Proteen Initiating Bone Differentiation"; Aug. 15, 1989; The Journal of Biological Chemistry, vol. 264, pp. 13377–13380.

U.S. patent application Ser. No. 07/720,174 filed Jun. 27, 1991 to U. Ripamonti.

Primary Examiner—David Isabella

[57] ABSTRACT

A method of preparing a delivery system for a biologically active growth and morphogenetic factor by using chromatographic techniques and which includes introducing such biologically active factor into a chromatography column of appropriate dimensions which contains a porous carrier comprising a solid adsorbent selected for its specific affinity for such biologically active factor. In one embodiment of the invention porous hydroxyapatite is used as the carrier for bone morphogenetic proteins (ie BMPs). The invention extends to a delivery system prepared according to the above method; to an apparatus for preparing the delivery system according to the method; and to use of the delivery system in a method for inducing the formation of new bone in primates.

4 Claims, 4 Drawing Sheets

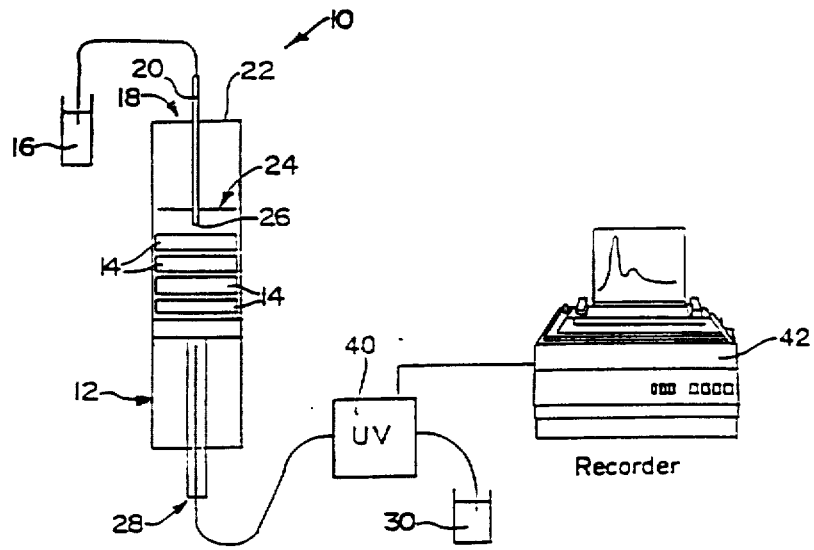

UNITED STATES PATENT AND TRADEMARK OFFICE
CERTIFICATE OF CORRECTION

Page 3 of 5

PATENT NO.    :    5,443,531

DATED    :    August 22, 1995

INVENTOR(S)    :    Ugo Ripamonti

It is certified that an error appears in the above-identified patent and that said Letters Patent is hereby corrected as shown below:

In the drawings, Sheet 1 of 4 should appear as follows:

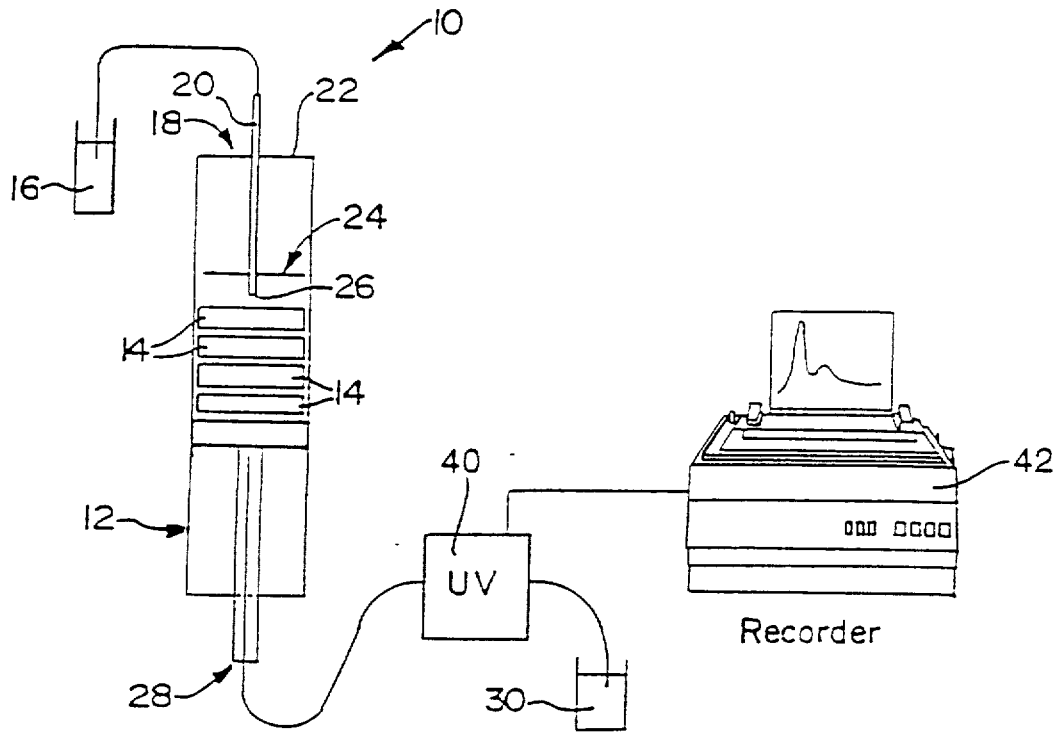

FIG 1

UNITED STATES PATENT AND TRADEMARK OFFICE
CERTIFICATE OF CORRECTION

PATENT NO. : 5,443,531

DATED : August 22, 1995

INVENTOR(S) : Ugo Ripamonti

It is certified that an error appears in the above-identified patent and that said Letters Patent is hereby corrected as shown below:

In the drawings, Sheet 4 of 4 should appear as follows:

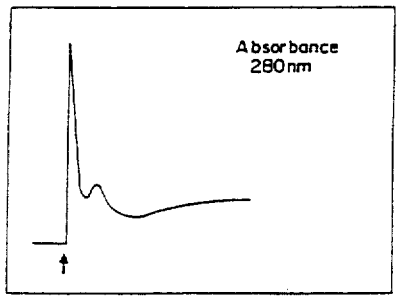

FIG 6

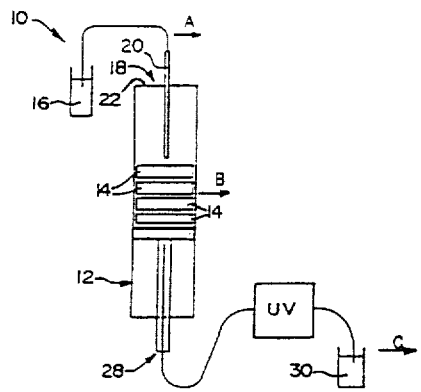

FIG 7

UNITED STATES PATENT AND TRADEMARK OFFICE
CERTIFICATE OF CORRECTION

PATENT NO. : 5,443,531
DATED : August 22, 1995
INVENTOR(S) : Ugo Ripamonti

It is certified that error appears in the above-indentified patent and that said Letters Patent is hereby corrected as shown below:

Column 8, line 8, should read as follows:

4. The method as claimed in claim 1, wherein step

Signed and Sealed this

Twenty-ninth Day of October 1996

Attest:

BRUCE LEHMAN

Attesting Officer

Commissioner of Patents and Trademarks